United States Patent [19]

Mitsuya et al.

[11] Patent Number: 4,879,277
[45] Date of Patent: Nov. 7, 1989

[54] ANTIVIRAL COMPOSITIONS AND METHODS

[75] Inventors: Hiroaki Mitsuya, Rockville; Samuel Broder; Robert Yarchoan, both Bethesda, all of Md.

[73] Assignee: The United States of America as represented by the Department of Health and Human Services, Washington, D.C.

[21] Appl. No.: 84,054

[22] Filed: Aug. 11, 1987

Related U.S. Application Data

[63] Continuation-in-part of Ser. No. 2,898, Jan. 13, 1987, abandoned, which is a continuation-in-part of Ser. No. 937,925, Dec. 4, 1986, abandoned, which is a continuation-in-part of Ser. No. 769,017, Aug. 26, 1985, abandoned.

[51] Int. Cl.$^4$ .................... A61K 31/70; C07D 473/16
[52] U.S. Cl. ...................... 514/49; 424/450; 514/43; 514/51; 514/78; 536/24
[58] Field of Search .............. 514/43, 49, 51, 78; 536/24; 424/450

[56] References Cited

U.S. PATENT DOCUMENTS 4,081,534  3/1978  Elion et al. ..................... 424/180
4,780,452 10/1988  Krenitsky et al. ................ 514/45

FOREIGN PATENT DOCUMENTS 206497 12/1986  European Pat. Off. .

Primary Examiner—A. Lionel Clingman
Attorney, Agent, or Firm—Browdy and Neimark

[57] ABSTRACT

Compositions containing 2',3'-dideoxycytidine and its triphosphates for use in treating retroviral infections including acquired immune deficiency syndrome (AIDS) are disclosed with preferred methods of treatment which provide protection against cytophatic effects of human immunodeficiency virus (HIV).

17 Claims, 3 Drawing Sheets

ANTIVIRAL COMPOSITIONS AND METHODS

This application is a continuation-in-part of Ser. No. 07/002,898, filed Jan. 13, 1987 (now pending); which is a continuation-in-part of Ser. No. 06/937,925, filed Dec. 4, 1986 (now abandonded); which is a continuation-in-part of Ser. No. 06/769,017, filed Aug. 26, 1985 (now abandonded).

The present invention relates to a method of treatment to prevent cytopathic effects of viruses. Of particular concern is protection against the cytopathic effects of HTLV-III/LAV (now known as Human Immunodeficiency Virus (HIV)), the causative agent of acquired immune disease syndrome (AIDS).

BACKGROUND OF THE INVENTION

The HIV virus which causes AIDS exerts a profound cytopathic effect on the helper/inducer T-cells, devastating the function of the immune system. The virus also shows a propensity to infect the brain with resulting neurological deterioration. The disease results in progressive debilitation and death. While several antiviral agents have been tested for use as a treatment of AIDS patients, no curative anti-retroviral agent has been found. See, for example, Mitsuya, H., et al., *Science*, 226, 172–174 (1984).

Broder, S. *AIDS: Modern Concepts and Therapeutic Challenges*, Marcer and Dekker, Inc., New York (1987).

Rosenbaum, W., et al., *Lancet*, i, 450–451 (1985).

McCormick, J. B., Getchell, J. P., Mitchell, S. W., & Hicks, D. R., *Lancet*, ii, 1367–1369 (1984).

Ho, D. D., et al, *Lancet*, i, 602–604 (1985).

Sandstrom, E. G., Kaplan, J. C., Byington, R. E., & Hirsch, M. S., *Lancet*, I, 1480–1482 (1985).

Azidothymidine (AZT) is presently being used for treatment of AIDS patients. However, the serious toxic side reactions and high cost of therapy present serious issues for those who would perscribe this drug on a continuing basis. There is an urgent need to devise other means of treatment for those with AIDS and other retroviral diseases. Any drug to be used in treatment of these chronically ill patients should, ideally, be available for oral administration and should penetrate the blood/brain barrier.

SUMMARY OF THE INVENTION

It is an object of the invention to provide therapeutic compositions and methods of treatment which overcome the deficiencies of the prior art compositions and methods of treatment cited above.

It is, futhermore, the object of the present invention to provide compositions and methods of treatment which may be useful in treating viral infections, particularly for treatment of AIDS patients.

It is a further object of the invention to provide means for intracellular delivery of the phosphorylated dideoxycytidine to infected cells.

While the exact mechanism of anti-viral activity of the compositions of the present invention is unknown, the probable mechanism involves modifying the naturally occuring 3'-carbon of the deoxyribose (of the viral RNA) so that it is not possible to form 5'-3' phosphodiester linkages necessary for DNA elongation in the replication of the virus from the RNA form to a DNA form. The present invention discloses the 2',3' dideoxycytidine is converted to a triphosphate by cellular enzymes, and the triphosphate product is used in transcription instead of 2'-deoxynucleoside-5'-triphosphate. The 2',3'-dideoxycytidine triphosphates act as DNA chain terminators, thus inhibiting DNA synthesis mediated by HIV reverse transcriptase and/or can act by competitively inhibiting the binding of the natural substrate for reverse transcriptase.

One embodiment of the present invention involves the direct delivery of the triphosphate derivative to the host cells. It is well known by practitioners in the art that "unshielded" triphosphates can not be used as drugs because triphosphate compounds do not penetrate cell membranes. Accordingly, the triphosphate derivatives of this invention may be delivered by means of liposomes, small particles (about 25 uM to 1 uM in diameter) which serve as intracellular transport systems to deliver normally non-absorbable drugs across the cell membrane. The use of liposomes for drug delivery is well known in the art and is based on a phospholipid's ability to spontaneously form bilayers in aqueous environments. One method of forming liposomes is by agitating phospholipids in aqueous suspensions at high frequencies. This results in the formation of closed vesicles characteristic of liposomes. Once inside the cells, the triphosphate derivatives act, as noted above, in the elimination of cytopathic effects of HIV. Since the triphosphate has been shown to be active inside the cells, and to be the active form therein, the liposome is clearly a method of choice for delivery of these drugs.

INFORMATION DISCLOSURE

Furmanski, et al., "Inhibition by 2',3'-Dideoxythymidine of Retroviral Infection of Mouse and Human Cells," *Cancer Letters*, 8: 307–315, 1980.

Wagar, et al., "Effects of 2'.3'-Dideoxynucleosides on Mammalian Cells and Viruses," *Journal of Cellular Physiology*, 121: 402–408 (1984).

SPECIFIC DESCRIPTION OF THE INVENTION

Figure 1:
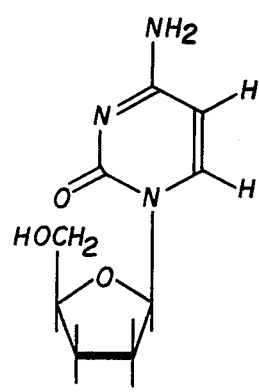
FIG. 1 shows the virustatic effect of 2'.3'-dideoxycytidine in vitro.
Figure 1:
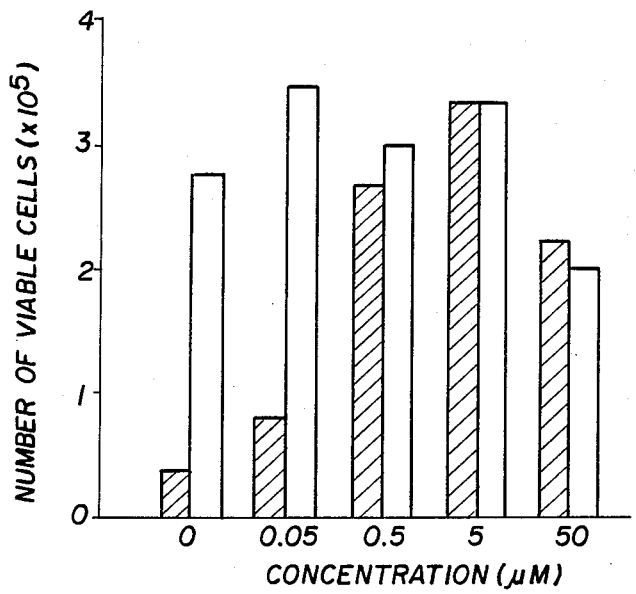

Active Ingredient:

The compositions of the present invention comprise a pyrimidine nucleoside with the ribose moiety of the molecule in the 2',3'-dideoxy configuration, and a pharmaceutically acceptable carrier. In the preferred embodiment, the active ingredient is 2',3'-dideoxycytidine, illustrated below:

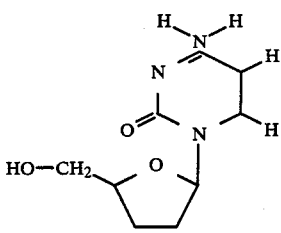

FORMULA 1

Preferred esters of the compound of formula (1) include carboxylic acid esters in which the non-carbonyl moiety of the ester grouping is selected from straight or branched chain alkyl, alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); sulphonate esters such as alkyl- or aralkylsulphonyl (e.g., methanesulphonyl); and mono-, di- or tri-phosphate esters.

Any reference to the above-described compounds also includes a reference to a pharmaceutically acceptable salt thereof with regard to the above-cited derivatives. Unless otherwise specified, any alkyl moiety present advantageously contains 1 to 18 carbon atoms, particularly 1 to 4 carbon atoms. Any aryl moiety present in such esters advantageously comprises a phenyl group, including a substituted phenyl group.

Examples of pharmaceutically acceptable salts of the compounds of formula (1) and pharmaceutically acceptable derivatives thereof include base salts, e.g., derived from an appropriate base, such as alkali metal (e.g., sodium), alkaline earth metal (e.g., magensium) salts, ammonium and $NX_4$ (wherein X is $C_{1-4}$ alkyl). Physiologically acceptable salts containing a hydrogen atom or an amino group include salts of organic carboxylic acids such as acetic, lactic, tartaric, malic, isothionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound containing any hydroxy group include the anion of said compound in combination with a suitable cation such as $Na^+$, $NHY_4^+$, and $HX_4^+$ (wherein X is a $C_{1-4}$ alkyl group.

Specific examples of pharmaceutically acceptable derivatives of the compound of formula (1) that may be used in accordance with the present invention include the monosodium salt and the following 5′ esters; monophosphate; disodium monophosphate; diphosphate; triphosphate; acetate; 3-methyl-butyrate; octanoate; palmitate; 3-chloro benzoate; benzoate; 4-methyl benzoate; hydrogen succinate; pivalate; and mesylate.

Also included within the scope of this invention are the pharmaceutically acceptable salts, esters, salts of such esters, nitrile oxides, or any other covalently linked or non-linked compound which, upon administration to the recipient, is capable of providing (directly or indirectly) a nucleoside analog as described above, or an anti-virally active metabolite or residue thereof. All of these compounds are active, and relatively non-toxic, at concentrations of sufficient potency for effective inhibition of viral infectivity and replication.

Pharmaceutically Acceptable Carrier:

It is possible for the nucleoside of the present invention to be administered alone in solution. However, in the preferred embodiment, the active ingredient(s) may be used or administered in a pharmaceutical formulation. These formulations comprise at least one active ingredient (the nucleoside), together with one or more pharmaceutically acceptable carriers and/or other therapeutic agents. As included within the scope of this invention, "acceptable" is defined as being compatible with other ingredients of the formulation and not injurious to the patient or host cell. These carriers include those well known to practitioners in the art as suitable for oral, rectal, nasal, topical, buccal, sublingual, vaginal, or parenteral (including subcutaneous, intramuscular, intravenous, and intradermal) administration. Specific carriers suitable for use in the invention are further defined below. With reference to the utilization of a pharmaceutically acceptable derivative. In the present case, it will be appreciated that the compounds according to the invention may also be used in the manufacture of pharmaceuticals for the treatment or prophylaxis of viral infections.

Administration:

The administration of 2′,3′-dideoxycytidine to humans suffering from AIDS illness, under conditions which effectively interrupt or suppress activity of the HIV virus, can be accomplished by one or more of several means of administration. In the preferred embodiment, whatever administrative method is chosen should result in circulating levels of the 2′,3′-dideoxycylidine within a range of about 0.05 uM to about 1.0 uM. A range of about 0.01–0.25 mg/kg given every 4 hours is considered a virustatic range in most large mammals. In order to achieve this, the preliminary dosage range for oral administration, is slightly broader, being for example, 0.005–0.25 mg/kg given every 4 hours. It is recognized that dose modifications might need to be made in individual patients to ameliorate or forestall toxic side effects.

The formulations may conveniently be presented in unit dosage form and may be prepared by any methods known in the pharmaceutical art. Such methods include the preparation of the active ingredient in a carrier which may contain additional medicinally active ingredients.

A preferred method of oral administration of the 2′,3′-dideoxycytidines of the present invention consists of dissolving an effective amount of the 2′,3′-dideoxycytidine in a sodium chloride solution, preferably 0.9% sodium chloride in orange juice. The 2′,3′-dideoxynucleosides may also be administered in tablet form, and may include one or more of the following: lactose (hydrous, fast flow), microcrystalline cellulose, colloidal silicon dioxide, croscarmellose sodium, magnesium stearate, stearic acid, and other excipients, colorants, and pharmacologically compatible carriers. Compositions for oral use may be administered to patients in fasting or non-fasting state.

Formulations of the present invention suitable for oral administration (including sustained release formulations) may be presented as discrete units such as capsules, cachets or tablets, each containing a predetermined amount of the active ingredient; as a powder or granules; as a solution or a suspension in an aqueous liquid; in an oil-in-water liquid emulsion or a water-in-oil liquid emulsion. The active ingredient may also be presented as a bolus, electurary or paste. Tablets may, if desired, be enteric coated.

The bioavailability of 2′,3′-dideoxycytidine was unexpected since analogues of cytidine are frequently destroyed by cytidine deaminase and related enzymes in the gastrointestinal system. Since the dideoxycytidine compositions of the instantly claimed invention are not sensitive to cytidine deaminase, oral administration of the compositions is appropriate.

Formulations suitable for topical administration include lozenges comprising the active ingredient in a flavor, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams, or spray formulas containing in addition to the active ingredient such carriers as are known in the art to be appropriate.

Formulations suitable for parenteral administration include aqueous and non-aqueous, isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Where either the oral or intravenous route is utilized, the medication is usually given three to six times a day. See Example 4 and FIGS. 2, 3, and in general, FIG. 1.

To improve oral bioavailability, it is often preferable to add a common buffer such as sodium acetate to a solution containing an active antiviral of the invention.

The administered ingredients may also be used in therapy in conjunction with other anti-viral drugs and biologicals, or in conjunction with other immune modulating therapy including bone marrow or lymphocyte transplants or medications.

EXAMPLES

EXAMPLE 1

Figure 2:
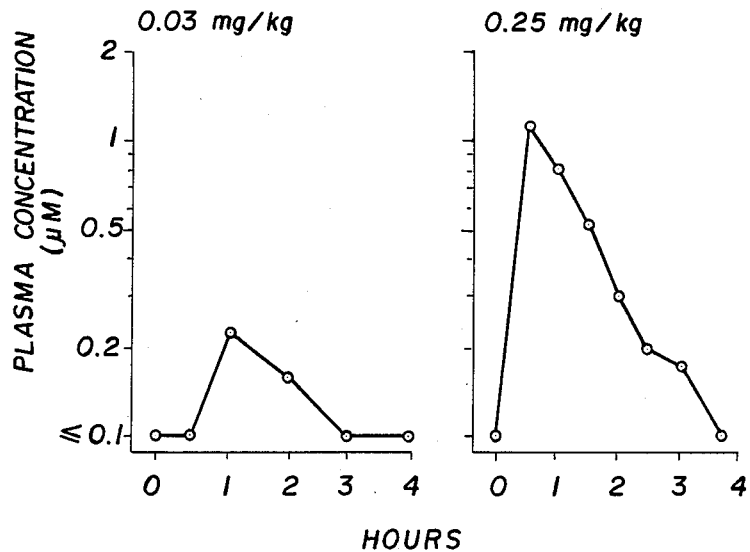
FIG. 2 shows plasma concentrations of 2'.3'-dideoxycytidine (ddC) against time, in hours, utilizing 0.03 mg/kg (left) and 0.25 mg/kg (right) during and after intravenous infusion in human beings infected by HIV with AIDS and related retroviral diseases.

FIG. 2 illustrates plasma concentrations of 2',3'-dideoxycytidine during and after a one-hour intravenous infusion of 2',3'-dideoxycytidine. Patients with HIV (HTLV-III) infection were given a one hour intravenous infusion of 0.03 mg/kg (left) or 0.25 mg/kg (right) of 2',3'-dideoxycytidine, and the plasma concentration of 2',3'-dideoxycytidine measured by high-performance liquid chromatography (HPLC). Each graph shows the plasma concentration measured in a different patient.

Example 2

Figure 3:
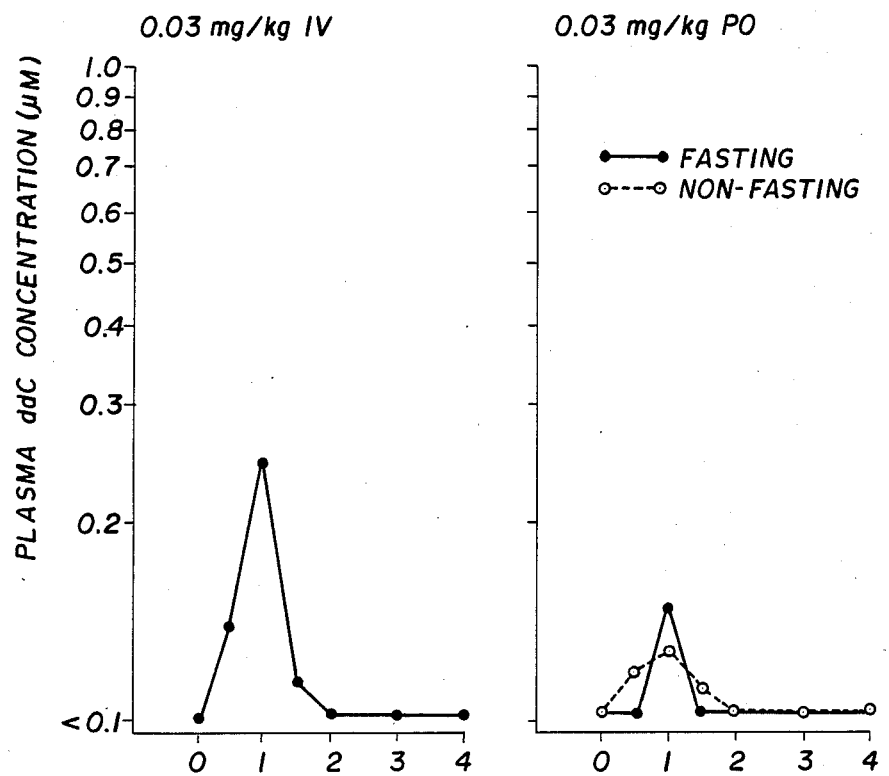
FIG. 3 shows plasma concentrations of 2',3'-dideoxycytidine (ddC) against time, in hours, showing fasting and non-fasting levels for the oral dosage (right) and for the IV (intravenous) infusion dosage (left).

FIG. 3 shows concentrations of 2',3'-dideoxycytidine during and after a one hour intravenous infusion or after oral administration of 2',3'-dideoxycytidine. A patient with HIV infection was given 0.03 mg/kg of 2',3'-dideoxycytidine by a one hour intravenous infusion (left) or by mouth dissolved in 0.1 ml of 0.9% sodium choloride and approximately 100 ml of orange juice. 2',3'-dideoxycytidine was given orally both while the patient was fasting (●—●) and after a meal (non-fasting) (0 - - - 0). Plasma concentrations of 2',3'-dideoxycytidine were determined at various time points by HPLC.

Example 3

In vitro inhibition of the cytopathic effect of human immunodeficiency disease virus ((HIV).

Figure 4:
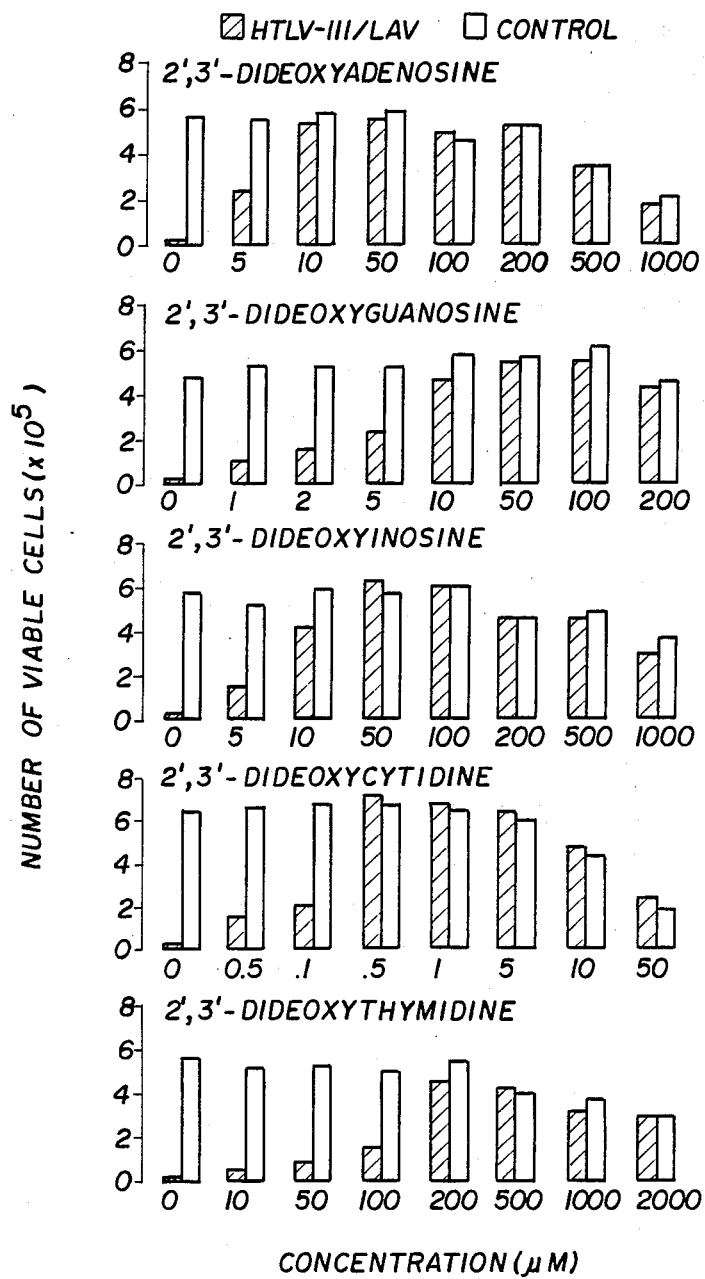
FIG. 4(a, b) shows the in vitro inhibition of the cytopathic effect of HIV by 2',3'-dideoxycytidine.

The compositions of the present invention were tested on ATH8 cells, a tetanus toxoid-specific T-cell line which exhibits rapid growth (in the presence of interleukin-2) and exquisite sensitivity to the cytopathic effect of HIV. ATH8 cells ($2 \times 10^5$) were pre-exposed to polybrene, and exposed to HIV in culture tubes (2,000 virus particles per cell), in the presence or absence of various concentrations of 2',3'-dideoxycytidine (ddC). The culture tubes contained 15% (vol/vol) interleukin-2 and 2 ml complete medium (RPMI supplemented with 15% undialyzed, heat-inactivated fetal calf serum, 4 mM L-glutamine, $5 \times 10^{-5}$ 2-mercaptoethanol, 50 U/ml penicillin, and 50 ug/ml streptomycin. The culture tubes were incubated at 37° C. and on day 5, the total number of viable cells were counted. Control cells were similarly treated, but were not exposed to the virus. The total number of viable cells, counted by the trypan blue dye exclusion method, are illustrated in FIG. 4-A, and shows the almost complete inhibition of the cytopathic effect of HIV.

The in vitro inhibition of the infectivity and replication of the HIV virus by ddC was also tested. The results are shown in FIG. 4-B. In this test, $10^5$ H9 cells were exposed to various concentrations of ddC for 4 hours, then to 2 ug/ml polybrene for 30 minutes, pelleted, and then exposed to HIV (3,000 virus particles/cell) for 1.5 hours. Cells were resuspended in fresh complete medium and cultured in tubes at 37° C. in 5% $CO_2$-containing humidified air, and under conditions in which the cells were continuously exposed to ddC. On days 8 (left), 9 (middle), and 10 (right) in culture, the percentage of the target H9 cells expressing p24 gag protein of HIV was determined by indirect immunofluorescence microscopy by using anti-HIV p24 murine monocolonal antibody. FIG. 4-B shows the almost complete inhibition of the infectivity and replication of HIV.

Example 5

The efficacy of the application of 2',3'-dideoxycytidine in human use is shown graphically in Table I, where the absolute number of T4 cells and the T4/T8 ratio both show an increase in the T cells, indicating improvements of the immune system in patients with AIDS and its related conditions following therapy. The studies of anabolic phosphorylation on human cells have concluded that comparable dosages are safe and non-lethal to T cells. It has also been shown that the circulating p24 antigen-level (a measure of viral replication in a patient's body) falls, following treatment with these compositions.

Toxicity toward humans has been shown by the observation residing in Table II. One toxic effect is bone marrow suppression (decreased platelets). Minor toxicities include skin rash and aphthous stomatitis. Some patients may also develop small fiber peripheral neuropathy with prolonged administration.

TABLE I

Increases in the Absolute Number of T4 Cells and T4/T8 Ratios in Two AIDS Patients Receiving 2',3'-dideoxycytidine (ddC)

| Pt. | Dose* | Number of Days** Receiving ddC | Start Treatment T4/mm3 | Start Treatment T4/T8 Ratio | End Treatment T/mm3 | End Treatment T4/T8 Ratio |
|---|---|---|---|---|---|---|
| 1 | 0.25 mg/kg | 8 | 309 | 0.20 | 530 | 0.40 |
| 2 | 0.03 mg/kg | 19 | 260 | 0.39 | 326 | 0.47 |
| 3 | 0.03 mg/kg | 12 | 246 | 0.26 | 307 | 0.51 |

*Patients 1 and 2 received one dose of ddC every 8 hours, and patient 3 received one dose every 4 hours. Patient 1 received intravenous (IV) dosing throughout; patient 2 received IV dosing for 21 days, followed by oral dosing; patient 3 received IV dosing throughout. IV dosing was given as 1 hour infusions. For oral dosing, the ddC was administered dissolved in 0.1 ml of 0.9% sodium chloride solution and approximately 100 ml of orange juice. Each patient received a 1 hour intravenous infusion (test dose) of ddC two days prior to the initiating of dosing.
**Note patients can exhibit a 50% to 100% reduction of HIV p24 antigen levels in the blood after one to two weeks of treatment.

TABLE II

Toxicity Observed Which is Likely to be Due to ddC Administration

| Dose | Toxicity |
|---|---|
| 0.25 mg/kg 3×/day intravenous | Thrombocytopenia (platelets dropped from 234,000/mm³ to 68,000/mm³); skin rash |
| 0.03 mg/kg 3×/day intravenous for 12 days followed by 0.3 mg/kg 3×/day orally | Tolerated for up to 40 days without significant toxicity in some patients; minor toxicity of skin rash and oral ulcers in one patient. |
| 0.03 mg/kg 6×/day intravenous for 14 days, followed by 0.03 mg/kg 6×/day orally | Tolerated for up to 18 days without significant toxicity. |

TABLE III

Anabolism of 2',3'-dideoxycytidine (ddCyd) by Human and Murine Cells*

| Cell Line | Intracellular concentration (uM) in cells exposed to 1 uM ddCyd for 24 hours. | | | | |
|---|---|---|---|---|---|
| | ddCyd | ddCMP | ddCDPch | ddCDP | ddCTP |
| Human T4+ T lymphocytes (ATH8 cell line) | 6.40 | 2.10 | 1.10 | 1.20 | 0.5 |
| Murine fibroblasts (NIH 3T3 cells) | 0.87 | 0.02 | 0.01 | 0.09 | 0.04 |

* After incubation with ³H-labelled 2',3'-dideoxycytidine (ddCyd) (1 uM) for 24 hr, cell cultures were added with 10% TCA; extracts were neutralized with tri-n octylamine in freon and were analyzed by ion exchange HPLC using radial compression columns of Partisil-SAX equilibrated and developed with 0.01 M ammonium phosphate, pH 3.6 for 15 min, followed by a linear gradient to 0.6 M ammonium phosphate, pH 3.8 over the next 25 min, and finally by a 5 min isocratic elution with 0.6 M ammonium phosphate, pH 3.8. ddCMP, 2',3'-dideoxycytidine-5'-monophosphate; ddCDP, 2',3'-dideoxy-5'-diphosphate; ddCDPch, 2',3'-CDP-choline; ddCTP, 2',3'-dideoxy-cytidine-5'-triphosphate. Note that in human cells a significant amount of 2',3'-dideoxycytidine-5'- triphosphate is formed; whereas this is not the case in mouse cells.

Example 6

Of critical importance to the biological activation of the 2',3'-dideoxycytidine analogues inside human cells, both as antiviral and as antitumor agents, is their anabolic conversion to nucleotides inside cells. This cannot be assumed to occur because not all nucleoside analgoues can be adequately phosphorylated. The ability of HIV-infected human T-lymphoblasts to phosphorylate 2',3'-dideoxycytidine nucleoside (ddCyd) was tested. ATH8 cells ($2 \times 10^7$ cells) were exposed to HIV at a dose of 3000 virus particles per cell; 24 hours later, [5-³H]ddCyd was added at a drug concentration of 1 uM, a level sufficient to result in 100% inhibition of the cytopathic effect, infectivity, and replication of the virus, but without cytotoxic effect on the host cells. The incubation was terminated after 24 hours of drug exposure, and the TCA-soluble fraction of the cell lysate was resolved on HPLC, utilizing a radial compression column of Partisil-10 SAX with a gradient of ammonium phosphate. Detected in the eluate were the parent nucleoside (48% of eluted radioactivity in a typical experiment), its mono-, di-, and tri-phosphate (17%, 13%, and 9%), and a peak of ³H-radioactivity appearing between ddCMP and ddCDP (prepard by hydrolysis of ddCTP by venom phosphodiesterase). No significant qualitative or quantitative differences were detected between uninfected and HIV-infected ATH8 cells in ability to phosphorylate ddCYD. However, when the physiological nucleoside dCYD (5 uM) was added together with ddCYD, phosphorylation was blocked, a result compatible with the observation that dCYD reverses the anti-HIV effect of ddCyd (see Table III).

Example 7

Effect of 2',3'-dideoxycytidine on the in vitro immune reactivity of normal lymphocytes: concentration (uM) of ddC brought about virtually complete inhibition of the cytopathic effect of HIV and the viral p24 expression. $5 \times 10^4$ normal helper/inducer TM3 cells were stimulated with tetanus toxoid (0.6 limiting flocculation units/ml) plus $10^5$ irradiated (4,000 rad) autologous peripheral blood mononuclear cells (PBM) as a source of accessory cells, and were cultured for 72 hours in the presence or absence of ddC. After exposure to uCi ³H-uridine for the final 5 hours, cells were harvested onto glass fibers and the incorporated radioactivity was counted. Data are expressed as the arithmetic mean counts per minute ($\times 10^3$)±1 standard deviation triplicate determinations. $10^6$ PBM from a healthy individual were stimulated with phytohaemagglutinin (PHA) or pokeweek mitogen (PWM) and cultured for 72 hours, and treated as described above. ³H-uridine incorporation was used as an indicator of activiation of the responder cells. These data show cells are not harmed by drug concentrations that exceed the virustatic dose.

| Responder Cells | ddC 1 uM | 10 uM | None |
|---|---|---|---|
| Clone TM 3 | 13 ± 1 | 8 ± 1 | 12 ± 1 |
| PBM + PHA | 101 ± 1 | 86 ± 3 | 82 ± 1 |
| PBM + PWM | 23 ± 3 | 15 ± 3 | 24 ± 1 |

What is claimed is:

1. A method for treating a patient infected with HIV comprising administering to said patient an effective amount of a composition comprising 2',3'-dideoxycytidine, a salt, or an ester thereof in a pharmaceutically acceptable carrier.

2. The method of claim 1 wherein the 2',3'-dideoxycytidine is in the form of the triphosphate and the carrier is suitable for intracellular administration.

3. The method of claim 1 wherein the pharmaceutically acceptable carrier is normal saline.

4. The method of claim 2 wherein the 2',3'-dideoxycytidine triphosphate is contained in a liposome.

5. The method of claim 1 wherein the 2',3'-dideoxycytidine is phosphorylated and the carrier is a liposome.

6. The method of claim 5 wherein the phosphorylated 2',3'-dideoxycytidine is a triphosphate.

7. A method for alleviating the cytopathic destructive effects of a retroviral disease in a patient infected with a retrovirus comprising administering to said patient an effective amount of an antiviral composition comprising 2',3'-dideoxycytidine, a salt, or an ester thereof in a pharmaceutically acceptable carrier.

8. A method of claim 7 wherein the retrovirus is HIV.

9. A method of claim 7 wherein dosage is 0.03–0.5 mg/kg administered 4–12 times a day.

10. A method of claim 7 wherein the medication is administered orally.

11. A method of claim 7 wherein the medication is administered intravenously.

12. A method of claim 11 wherein the medication is infused continuous.

13. A method of claim 7 wherein the method of administration is selected from the group consisting of rectally, nasally, or vaginally.

14. A method of claim 7 wherein said effective amount of 2',3'-dideoxycytidine is administered in orange juice with sodium chloride.

15. A method of claim 7 wherein the composition is administered intravenously in an amount of about 0.03 to about 0.25 mg/kg body wieght.

16. A method of claim 7 wherein the composition is administered orally in an amount of 0.06 to about 0.5 mg/kg.

17. A method for alleviating the cytopathic destructive effects of a retroviral disease in a patient infected with a retrovirus comprising administering to said patient a viral suppressing effective amount of an antiviral composition comprising 2',3'-dideoxycytidine in a liposome carrier.

* * * * *